(12) United States Patent
Chang (10) Patent No.: US 9,931,505 B1
(45) Date of Patent: Apr. 3, 2018

(54) SYSTEM AND METHOD FOR PROMOTING IMMUNITY OF ANIMAL OR HUMAN

(71) Applicant: Wen-Chieh Chang, Taichung (TW)

(72) Inventor: Wen-Chieh Chang, Taichung (TW)

(73) Assignee: Taiwan Resonant Waves Research Corp., Taipei (TW)

( * ) Notice: Subject to any disclaimer, the term of this patent is extended or adjusted under 35 U.S.C. 154(b) by 78 days.

(21) Appl. No.: 15/264,607

(22) Filed: Sep. 14, 2016

(51) Int. Cl.
*A61N 1/00* (2006.01)
*A61N 1/36* (2006.01)
*A61N 1/04* (2006.01)

(52) U.S. Cl.
CPC ....... *A61N 1/36014* (2013.01); *A61N 1/0492* (2013.01)

(58) Field of Classification Search
CPC ........ A61N 1/18; A61N 1/32; A61N 1/36014; A61N 1/40; A61N 12/004; A61N 5/00; A61N 5/06; A61N 5/02
See application file for complete search history.

(56) References Cited

U.S. PATENT DOCUMENTS

2017/0172842 A1* 6/2017 Chang .................. A61N 1/0456
2017/0312506 A1* 11/2017 Chang .................. A61N 1/0492

* cited by examiner

*Primary Examiner* — Scott Getzow (57) ABSTRACT

A system and method for promoting immunity of animals or human, which comprises an energy wave generator has an energy wave's frequency control mode. The energy wave's frequency control mode includes multiple controls for acting the energy wave generator to generate and emit energy waves each with a corresponding energy density. The energy density is calculated by a corresponding base frequency, a sweep bandwidth of the corresponding base frequency, an emission rate and a total time of emission in a duty cycle, so that the energy waves with the corresponding energy densities effecting on the body of animals or human to promote immunity of animals or human.

19 Claims, 5 Drawing Sheets

| Order | Ori. Fn Fo(hz) | Duty D(%) | Pluse Rate P(hz) | Time T(sec) | Program Time (min, sec) Signal Type | | | | | Width m | Total Time Tt(sec) | Energy Density ED | 252 SUM Norm | ED.A7 | ED.A1 | Average | filter | Lower limit | Upper limit | 3 <Lower limit | 3.5 >Upper limit |
|---|---|---|---|---|---|---|---|---|---|---|---|---|---|---|---|---|---|---|---|---|---|
| n | | | | | SF(1) | SD(2) | SI(3) | SC(4) | SE(5) | | | | | | | | | | | | |
| 1 | 22107 | 70 | 1 | 2 | 1 | 0 | 0 | 0 | 0 | 0 | 2 | 4.49 | 1.8% | 4.49 | 6.98 | 5.74 | 1 | 3.37 | 8.73 | 2.74 | 9.24 |
| 2 | 15036 | 70 | 1 | 7 | 1 | 0 | 0 | 0 | 0 | 0 | 7 | 4.87 | 1.9% | 4.87 | 6.88 | 5.87 | 1 | 3.65 | 8.60 | 2.87 | 9.37 |
| 3 | 10000 | 70 | 1 | 12 | 1 | 0 | 0 | 0 | 0 | 0 | 12 | 4.92 | 2.0% | 4.92 | 6.43 | 5.68 | 1 | 3.69 | 8.03 | 2.68 | 9.18 |
| 4 | 5000 | 70 | 1 | 21 | 1 | 0 | 0 | 0 | 0 | 0 | 21 | 4.87 | 1.9% | 4.87 | 6.38 | 5.63 | 1 | 3.65 | 7.98 | 2.63 | 9.13 |
| 5 | 4442 | 70 | 1 | 23 | 1 | 0 | 0 | 0 | 0 | 0 | 23 | 4.85 | 1.9% | 4.85 | 6.34 | 5.60 | 1 | 3.64 | 7.93 | 2.60 | 9.10 |
| 6 | 3175 | 70 | 1 | 9 | 0 | 0 | 3 | 0 | 0 | 2 | 27 | 5.26 | 2.1% | 5.26 | 6.30 | 5.78 | 1 | 3.94 | 7.88 | 2.78 | 9.28 |
| 7 | 3000 | 70 | 1 | 28 | 1 | 0 | 0 | 0 | 0 | 0 | 28 | 4.77 | 1.9% | 4.77 | 6.48 | 5.62 | 0 | 0.00 | 0.00 | 2.62 | 9.12 |
| 8 | 1153 | 70 | 1 | 13 | 0 | 2 | 0 | 0 | 0 | 2 | 39 | 4.98 | 2.0% | 4.98 | 6.41 | 5.69 | 0 | 0.00 | 0.00 | 2.69 | 9.19 |
| 9 | 1130 | 70 | 1 | 8 | 0 | 0 | 3 | 0 | 0 | 4 | 40 | 5.20 | 2.1% | 5.20 | 6.30 | 5.75 | 0 | 0.00 | 0.00 | 2.75 | 9.25 |
| 10 | 1016 | 70 | 1 | 42 | 1 | 0 | 0 | 0 | 0 | 0 | 42 | 4.48 | 1.8% | 4.48 | 6.12 | 5.30 | 0 | 0.00 | 0.00 | 2.30 | 8.80 |
| 11 | 2411 | 70 | 1 | 31 | 1 | 0 | 0 | 0 | 0 | 0 | 31 | 4.72 | 1.9% | 4.72 | 6.10 | 5.41 | 1 | 3.54 | 7.62 | 2.41 | 8.91 |
| 12 | 1972 | 70 | 1 | 33 | 1 | 0 | 0 | 0 | 0 | 0 | 33 | 4.66 | 1.8% | 4.66 | 6.10 | 5.38 | 1 | 3.49 | 7.63 | 2.38 | 8.88 |
| 13 | 1823 | 70 | 1 | 34 | 1 | 0 | 0 | 0 | 0 | 0 | 34 | 4.64 | 1.8% | 4.64 | 5.80 | 5.22 | 1 | 3.48 | 7.25 | 2.22 | 8.72 |
| 14 | 1644 | 70 | 1 | 36 | 1 | 0 | 0 | 0 | 0 | 0 | 36 | 4.62 | 1.8% | 4.62 | 6.90 | 5.76 | 1 | 3.46 | 8.63 | 2.76 | 9.26 |
| 15 | 1550 | 70 | 1 | 12 | 0 | 0 | 0 | 0 | 0 | 2 | 36 | 5.07 | 2.0% | 5.07 | 6.84 | 5.95 | 1 | 3.80 | 8.55 | 2.95 | 9.45 |
| 16 | 688 | 70 | 1 | 5 | 0 | 2 | 0 | 0 | 0 | 9 | 50 | 5.38 | 2.1% | 5.38 | 6.80 | 6.09 | 0 | 0.00 | 0.00 | 3.09 | 9.59 |
| 17 | 644 | 70 | 1 | 7 | 0 | 2 | 0 | 0 | 0 | 9 | 49 | 5.19 | 2.1% | 5.19 | 6.65 | 5.92 | 0 | 0.00 | 0.00 | 2.92 | 9.42 |
| 18 | 624 | 70 | 1 | 8 | 0 | 0 | 0 | 0 | 0 | 6 | 51 | 5.58 | 2.2% | 5.58 | 6.35 | 5.96 | 0 | 0.00 | 0.00 | 2.96 | 9.46 |
| 19 | 591 | 70 | 1 | 3 | 0 | 0 | 3 | 4 | 0 | 8 | 57 | 5.65 | 2.2% | 5.65 | 6.31 | 5.98 | 0 | 0.00 | 0.00 | 2.98 | 9.48 |
| 20 | 549 | 70 | 1 | 4 | 0 | 0 | 0 | 4 | 0 | 6 | 52 | 5.41 | 2.1% | 5.41 | 6.30 | 5.86 | 0 | 0.00 | 0.00 | 2.86 | 9.36 |
| 21 | 522 | 70 | 1 | 17 | 1 | 0 | 3 | 0 | 0 | 2 | 51 | 4.75 | 1.9% | 4.75 | 5.70 | 5.22 | 1 | 3.56 | 7.12 | 2.22 | 8.72 |
| 22 | 510 | 70 | 1 | 17 | 0 | 0 | 3 | 0 | 0 | 2 | 51 | 4.74 | 1.9% | 4.74 | 6.30 | 5.52 | 1 | 3.55 | 7.88 | 2.52 | 9.02 |
| 23 | 464 | 70 | 1 | 9 | 0 | 2 | 0 | 0 | 0 | 5 | 54 | 5.02 | 2.0% | 5.02 | 6.37 | 5.70 | 1 | 3.77 | 7.96 | 2.70 | 9.20 |
| 24 | 442 | 70 | 1 | 53 | 1 | 0 | 0 | 0 | 0 | 0 | 53 | 4.21 | 1.7% | 4.21 | 4.58 | 4.40 | 1 | 3.16 | 5.73 | 1.40 | 7.90 |
| 25 | 431 | 70 | 1 | 3 | 0 | 0 | 3 | 4 | 0 | 9 | 57 | 5.51 | 2.2% | 5.51 | 5.78 | 5.65 | 0 | 0.00 | 0.00 | 2.65 | 9.15 |
| 26 | 410 | 70 | 1 | 3 | 0 | 0 | 3 | 4 | 0 | 8 | 51 | 5.40 | 2.1% | 5.40 | 2.92 | 4.16 | 0 | 0.00 | 0.00 | 1.16 | 7.66 |
| 27 | 2128 | 70 | 1 | 10 | 1 | 0 | 0 | 0 | 0 | 5 | 110 | 6.26 | 2.5% | 6.26 | 0.00 | 3.13 | 0 | 0.00 | 0.00 | 0.13 | 6.63 |
| 28 | 987 | 70 | 1 | 42 | 0 | 0 | 0 | 0 | 0 | 0 | 42 | 4.46 | 1.8% | 4.46 | 0.00 | 2.23 | 0 | 0.00 | 0.00 | -0.77 | 5.73 |
| 29 | 933 | 70 | 1 | 4 | 0 | 0 | 3 | 4 | 0 | 9 | 40 | 5.42 | 2.1% | 5.42 | 0.00 | 2.71 | 0 | 0.00 | 0.00 | -0.29 | 6.21 |
| 30 | 880 | 70 | 1 | 5 | 0 | 2 | 0 | 0 | 0 | 7 | 40 | 5.29 | 2.1% | 5.29 | 0.00 | 2.65 | 0 | 0.00 | 0.00 | -0.35 | 6.15 |
| 31 | 860 | 70 | 1 | 3 | 0 | 0 | 3 | 4 | 0 | 8 | 45 | 5.61 | 2.2% | 5.61 | 0.00 | 2.80 | 1 | 0.00 | 7.01 | -0.20 | 6.30 |
| 32 | 823 | 70 | 1 | 5 | 0 | 0 | 3 | 0 | 0 | 6 | 45 | 5.37 | 2.1% | 5.37 | 0.00 | 2.68 | 1 | 0.00 | 6.71 | -0.32 | 6.18 |
| 33 | 801 | 70 | 1 | 3 | 0 | 0 | 0 | 4 | 0 | 7 | 39 | 5.45 | 2.2% | 5.45 | 0.00 | 2.73 | 1 | 0.00 | 6.82 | -0.27 | 6.23 |
| 34 | 781 | 70 | 1 | 3 | 0 | 0 | 3 | 0 | 0 | 8 | 45 | 5.57 | 2.2% | 5.57 | 0.00 | 2.78 | 1 | 0.00 | 6.96 | -0.22 | 6.28 |
| 35 | 758 | 70 | 1 | 4 | 0 | 2 | 0 | 0 | 0 | 9 | 51 | 5.66 | 2.2% | 5.66 | 0.00 | 2.83 | 0 | 0.00 | 0.00 | -0.17 | 6.33 |
| 36 | 736 | 70 | 1 | 3 | 0 | 0 | 0 | 4 | 0 | 9 | 38 | 5.57 | 2.2% | 5.57 | 0.00 | 2.79 | 0 | 0.00 | 0.00 | -0.21 | 6.29 |
| 37 | 696 | 70 | 1 | 2 | 0 | 0 | 0 | 4 | 0 | 5 | 38 | 5.55 | 2.2% | 5.55 | 0.00 | 2.77 | 0 | 0.00 | 0.00 | -0.23 | 6.27 |
| 38 | 2008 | 70 | 1 | 10 | 1 | 0 | 0 | 0 | 0 | 2 | 110 | 6.23 | 2.5% | 6.23 | 0.00 | 3.12 | 0 | 0.00 | 0.00 | 0.12 | 6.62 |
| 39 | 384 | 70 | 1 | 18 | 0 | 0 | 3 | 0 | 0 | 9 | 54 | 4.64 | 1.8% | 4.64 | 0.00 | 2.32 | 0 | 0.00 | 0.00 | -0.68 | 5.82 |
| 40 | 374 | 70 | 1 | 55 | 1 | 0 | 0 | 0 | 0 | 5 | 55 | 4.16 | 1.7% | 4.16 | 0.00 | 2.08 | 0 | 0.00 | 0.00 | -0.92 | 5.58 |
| 41 | 346 | 70 | 1 | 6 | 0 | 0 | 3 | 0 | 0 | 9 | 60 | 5.16 | 2.0% | 5.16 | 0.00 | 2.58 | 1 | 0.00 | 6.45 | -0.42 | 6.08 |
| 42 | 338 | 70 | 1 | 4 | 0 | 0 | 3 | 0 | 0 | 7 | 60 | 5.33 | 2.1% | 5.33 | 0.00 | 2.66 | 1 | 0.00 | 6.66 | -0.34 | 6.16 |
| 43 | 248 | 70 | 1 | 5 | 0 | 0 | 0 | 0 | 0 | 6 | 65 | 5.17 | 2.1% | 5.17 | 0.00 | 2.58 | 0 | 0.00 | 0.00 | -0.42 | 6.08 |
| 44 | 222 | 70 | 1 | 15 | 0 | 2 | 0 | 0 | 0 | 3 | 60 | 4.57 | 1.8% | 4.57 | 0.00 | 2.29 | 0 | 0.00 | 0.00 | -0.71 | 5.79 |
| 45 | 152 | 70 | 1 | 5 | 0 | 0 | 3 | 0 | 0 | 6 | 65 | 4.95 | 2.0% | 4.95 | 0.00 | 2.48 | 0 | 0.00 | 0.00 | -0.52 | 5.98 |
| 46 | 126 | 70 | 1 | 5 | 0 | 0 | 0 | 4 | 0 | 6 | 65 | 4.87 | 1.9% | 4.87 | 0.00 | 2.44 | 0 | 0.00 | 0.00 | -0.56 | 5.94 |
| 47 | 92 | 70 | 1 | 18 | 0 | 0 | 3 | 0 | 0 | 3 | 72 | 4.27 | 1.7% | 4.27 | 0.00 | 2.13 | 0 | 0.00 | 0.00 | -0.87 | 5.63 |
| 48 | 68 | 70 | 1 | 5 | 0 | 2 | 0 | 0 | 0 | 8 | 85 | 4.84 | 1.9% | 4.84 | 0.00 | 2.42 | 0 | 0.00 | 0.00 | -0.58 | 5.92 |
| 49 | 33 | 70 | 1 | 11 | 0 | 0 | 0 | 4 | 0 | 7 | 88 | 4.21 | 1.7% | 4.21 | 0.00 | 2.11 | 0 | 0.00 | 5.26 | -0.89 | 5.61 |
| 50 | 13 | 70 | 1 | 7 | 1 | 0 | 0 | 0 | 0 | 7 | 105 | 4.16 | 1.6% | 4.16 | 0.00 | 2.08 | 1 | 0.00 | 5.20 | -0.92 | 5.58 |

FIG.9

SYSTEM AND METHOD FOR PROMOTING IMMUNITY OF ANIMAL OR HUMAN

BACKGROUND OF THE INVENTION

1. Fields of the Invention

The present invention relates to a system and method for promoting immunity, and more particularly, to a technology for controlling and emitting energy waves to promote immunity of animal or human.

2. Descriptions of Related Art

As we known, immunity means the ability of human immune system to defense against bacteria. The human first immune system includes skin, as well as oral mucosa, nasal mucosa, etc., blocking the surface of the larger volume of the body to against bacteria. When some of the smaller substances or bacteria invade the body, the body's second immune system including the lymph, spleen, bone marrow, thymus and tonsils, etc., will begin their effect to manufacture and deliver immune cells and immune factors to generate defensive reactions throughout the body. In addition to against bacteria and viruses, the immune system can also clear the body of cell damage degeneration and aging, and remove metabolic waste to maintain a stable internal environment of the body. The reasons of decreased immunity in addition to aging, include poor living conditions, irregular lifestyle, smoking, malnutrition or nutrition, mental stress and other factors. Most generally, the elderly and children are in immunocompromised state. Especially in the elderly bodies, their organ function begins to decline resulting in decreased ability to obtain nutrients, coupled with the decline of immune organs gradually atrophy, and then their immunities decrease indeed. When the immune system of one's declines, the most direct responses are relatively easy to get sick requiring lengthy training before being restored to a healthy state, and very easy to relapse. As for other symptoms such as wound is susceptible, fatigue, poor sleep quality, indigestion and listlessness etc. are the information of decreased immunity of the human body. Until now, not yet have a drug treatment method can effectively enhance immunity. The way to boost the immune system at this stage, mostly just are trying to require patients in regular lifestyle to improve quality of sleep, having a balanced diet and nutritional supplements (such as the B, E vitamins and minerals). To require the patient to achieve the above requirement, in fact, is not very easy, that is the important reason that the immunity of the patients can't be effectively promoted.

To apply wave energy in sound, electromagnetic or optical form effecting on plant, animal or human, to promote cell growth, or inhibit the growth of foreign cells, or produce specific physiological or psychological treatment or soothing, is currently quite universally endorsed technology and research. But currently available conventional arts, are only roughly using a simple fixed frequency wave energy (such as low-frequency fixed-frequency, medium frequency or high frequency, etc.) to act on the human body, they are not in-depth studied to know and have what kind energy wave with frequencies spectrum combination is effective for corresponding diseases and physical discomfort, and they are only rough frequency energy wave regardless what kind illness or physical discomfort to be applied for, so the effects of treatment or relieve of symptoms must be unable to effectively highlight.

According to the theory of quantum medicine, all living things and life forms have their own physiological frequency (which is the biological resonant wave), and harmonized wave frequency occurs in healthy human bodies. On the other hand, a disordered wave frequency occurred in human body indicates functional degradation of the living thing and sickness caused by a harmonic interference of diseases or viruses. In 1930, American physicist, Royal Rife, discovered that every object contains bacteria and viruses having their own natural frequency, and such discovery was used by doctors of University of Southern California for medical tests in 1934 and satisfactory results were achieved. Royal Rife's research discovered that different resonant waves have different physiological reactions to human body. Thereafter, a Canadian corporation, Resonant Light Technology Inc. developed a resonant wave health instrument for measuring the physiological frequency of a human body. The electric energy wave emitted from the instrument has a wavelength of 4-20 microns (um), which is very close to the wavelength of the biological wave of a human body (3~45 um), so as to provide a healthcare function to human body. At present, researches on the subject of treating cancers by electromagnetic waves are conducted extensively. Although the prior art has introduced electric energy waves into human body to produce resonance with the physiological frequency of human body, so as to achieve the treatment effect, yet the conventional techniques or researches do not use the electric energy wave technology to create a frequency modulation treatment formulation for promoting immunity of animal and human effectively.

Since the biological resonant waves probably have high efficacy in improvement of physiological faculty and curing diseases, and the inventor of the present patent application has researched for a long time to apply the resonant energy wave to improve some kinds of physiological faculty and cure some diseases. The inventor had an invention of system and method for emitting energy wave by specific frequency controls to reduce or eliminate high blood sugar factor of diabetes, and such invention had been issued for Taiwanese patent No. 1453046 and U.S. Pat. No. 9,421,368. After the aforementioned invention, the inventor of the present patent application put into research applying such specific controls to emit energy wave with specific energy density to promote immunity of animal and human.

SUMMARY OF THE INVENTION

The primary objective of the present invention is to provide a system and method for promoting immunity of animal or human. The system comprises an energy wave generator having an energy wave's frequency control mode for controlling and generating energy waves. The energy wave's frequency control mode comprising multiple controls in multiple energy wave generation periods respectively. The multiple controls act the energy wave generator to generate and emit energy waves each with a corresponding energy density having a value between 0.00~8.93 by a corresponding base frequency between 1~22200 Hz to effect on bodies of animals or human so as to promote immunities of the animals or human. The control modes are at least one fixed frequency sweep mode and at least one adjusted frequency sweep mode. The energy density of each energy wave is calculated by the following formula: ED=log 10 (freq.×D %×(2 Width+1)×(TT)+1), wherein freq., Width, D % and TT represent the base frequency, the predetermined sweep bandwidth, an emission rate and a total time of emission in a duty cycle of the base frequency respectively.

BRIEF DESCRIPTION OF THE DRAWINGS

FIG. 9 is a schematic view of list of relations between spectrums of effect frequencies, modulation parameters and energy densities of the present invention.

DETAILED DESCRIPTION OF THE PREFERRED EMBODIMENT

Referring to FIGS. 1 to 6, the system of the present invention comprises an energy wave generator 10. The energy wave generator 10 is set an energy wave's frequency control mode. The energy wave generator 10 generates and emits energy waves (i.e. resonant wave) according to the control of the energy wave's frequency control mode. In one embodiment of the present invention, the energy wave's frequency control mode includes first to sixth sets of controls in corresponding first to sixth sets of energy wave generation periods. The energy wave generator 10 generates and emits the energy waves each with a corresponding energy density by a corresponding frequency sweep mode based on a base frequency in the first to sixth energy wave generation periods respectively according to the controls of the energy wave's frequency control mode, so that the energy waves effect on the body of animal or human to promote immunity of animals or human.

Figure 1:
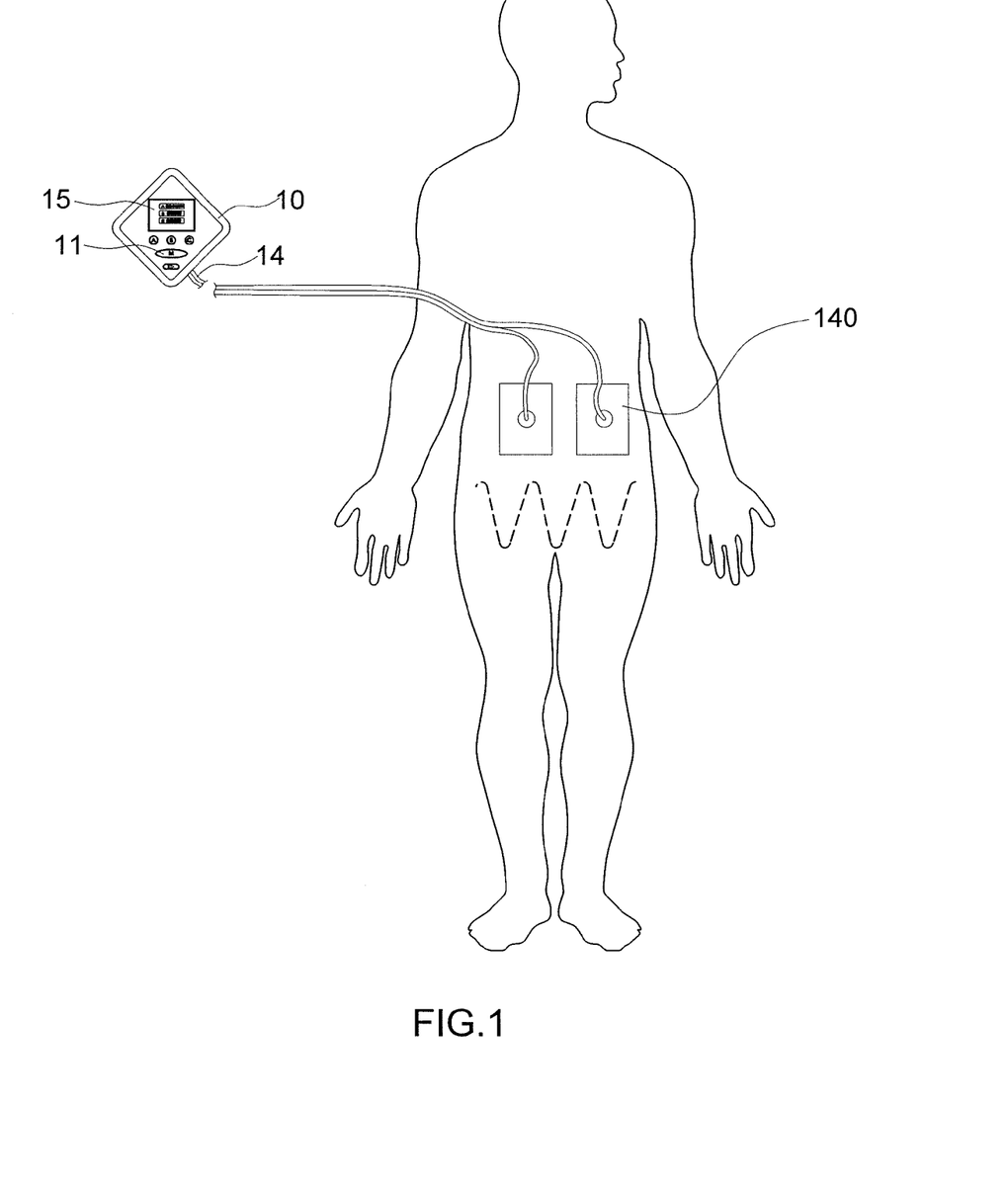
FIG. 1 is a schematic view of the system of the present invention.
Figure 2:
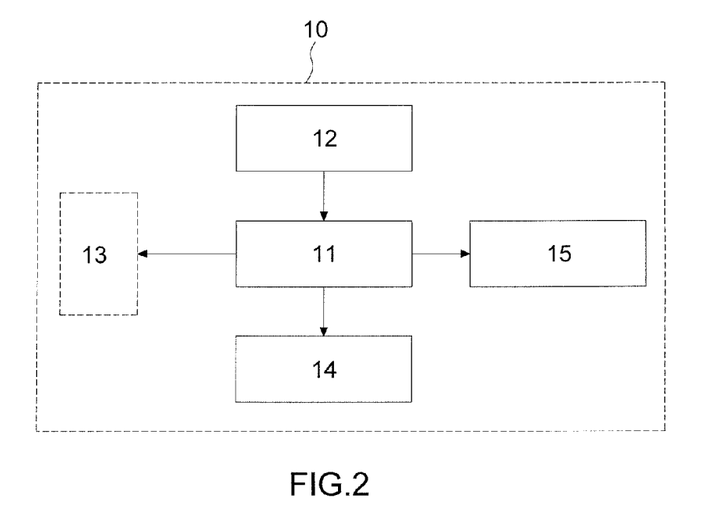
FIG. 2 is a schematic block diagram of units of the system of the present invention.

Referring to FIGS. 1 to 2, the energy wave generator 10 comprises a user interface 12, a control unit 11, a database 13 for saving the information of spectrums of effect frequency and modulation parameters corresponding to each effect frequency used in each energy wave generation periods, an energy wave output unit 14 and a display unit 15. In one embodiment of the present invention, the energy waves are in electric forms, and the energy wave output unit 14 includes a set of electrode sheets 140 for affixing to the body of diabetes so as to construct a circulation loop between the body and the electrical energy wave output unit 14 to transmit electric energy waves to the body of diabetes. The control unit 11 (such as a combination of microcontroller and driving circuit) sequentially reads the information of spectrums and modulation parameters of effect frequencies in the database 13, and then drives the energy wave output unit 14 to sequentially generates and emits electric energy waves each with a respective energy density (ED) in each corresponding energy wave generation period.

The control unit 11 of the present invention can be triggered to read the associated information of spectrums and modulation parameters in the database 13 by the command signals generated from the user interface 12, and then generates driving signals to control the energy wave output unit 14 (such as weak pulse generating circuit, voltage≤10V, current≤5 mA) switching on and off according to the corresponding frequencies, so that the energy wave output unit 14 generates corresponding electric energy waves with corresponding energy densities in required distributions of values in the corresponding energy wave generation periods. The display unit 15 is used to display the status of operation or procession of the system. Further, the embodiment of the present invention, the energy wave output unit 14 is not to be limited to a weak pulse generating circuit, the energy wave output unit 14 also may be a light emitting device or an audio play device enabling the energy wave generator system 10 to emits energy waves in light form or audio form in required corresponding frequencies.

In one embodiment of the invention, the energy wave generator 10 according to the control of the energy wave's frequency control mode sequentially outputs the energy waves from first to sixth energy wave generation periods. The controls of the energy wave's frequency control mode are for: (a) continuously and sequentially generating a 1st to a 6th energy waves with a corresponding 1st to a 6th energy densities by a corresponding 1st to a 6th base frequencies respectively in the first energy wave generation period, wherein, the 1st energy density of the 1st energy wave is between 3.37~8.73 (preferably 4.49), the 2nd energy density of the 2nd energy wave is between 3.65~8.60 (preferably 4.87), the 3rd energy density of the 3rd energy wave is between 3.69~8.03 (preferably 4.92), the 4th energy density of the 4th energy wave is between 3.65~7.98 (preferably 4.87), the 5th energy density of the 4th energy wave is between 3.64~7.93 (preferably 4.85) and the 6th energy density of the 4th energy wave is between 3.94~7.88 (preferably 5.26); (b) continuously and sequentially generating a 7th to a 11th energy waves with corresponding a 7th to a 11th energy densities by a 7th to a 11th base frequencies respectively in the second energy wave generation period, wherein, the 7th energy density is between 3.54~7.62 (preferably 4.72), the 8th energy density between 3.49~7.63 (preferably 4.66), the 9th energy density is between 3.48~7.25 (preferably 4.64), the 10th energy density is between 3.46~8.63 (preferably 4.62) and the 11th energy density is between 3.80~8.55 (preferably 5.07); (c) continuously and sequentially generating a 12th to a 15th energy waves with a 12th to a 15th energy densities by a 12th to a 15th base frequencies respectively in the third energy wave generation period, wherein, the 12th energy density is between 3.56~7.12 (preferably 4.75), the 13th energy density is between 3.55~7.88 (preferably 4.74), the 14th energy density is between 3.77~7.96 (preferably 5.02) and the 15th energy density is between 3.16~5.73 (preferably 4.21); (d) continuously and sequentially generating a 16th to a 19th energy waves with a 16th to a 19th energy densities by a 16th to a 19th base frequencies respectively in the fourth energy wave generation period, wherein, the 16th energy density is between 0.00~7.01 (preferably 5.61), the 17th energy density is between 0.00~6.71 (preferably 5.37), the 18th energy density is between 0.00~6.82 (preferably 5.45) and the 19th energy density is between 0.00~6.96 (preferably 5.57); (e) continuously and sequentially generating a 20th to a 22nd energy waves with a 20th to a 22nd energy densities by a 20th to a 22nd base frequencies respectively in the fifth energy wave generation period, wherein, the 20th energy density is between 0.00~6.45 (preferably 5.16), the 21st energy density is between 0.00·6.66 (preferably 5.33) and the 22nd the energy density is between 0.00 and 6.46 (preferably 5.17); (f) continuously and sequentially generating a 23rd to a 24th energy waves with a 23rd to a 24th energy densities by a 23rd to a 24th base frequencies respectively in the sixth energy wave generation period, wherein, the 23rd energy density is between 0.00~5.26 (preferably 4.21) and the 24th energy density is between 0.00~5.20 (preferably 4.16).

The value of aforementioned energy densities of the energy waves by their corresponding frequencies are calculated by the formula: $ED=\log 10$ (base freq.$\times D\% \times (2\ Width+1) \times (TT)+1)$. For example of the 1st base frequency in the first energy wave generation period, if we set the 1st base freq.=22113.7 Hz, the emission rate in a duty cycle (D %)=70%, the sweep bandwidth (Width) (m)=0 Hz and the total time of emission (TT)=2 secs in a duty cycle, and then the energy density (ED)=$\log 10$ $(22113.7 \times 70\% \times (2 \times 0+1) \times 2+1)=4.49$. Although there is no specific unit referring to the energy density (ED) of the present invention, the ED has real meaning, which represents a total transmit power of energy wave. When the frequency is higher, the times of switch voltage (current) is more, and energy used is more. The total time of emission means the duration of effect energy wave. The value of ED has been taken into account with all transmission parameters, which is on behalf of transmitting behavior. If each parameter is changed too large, the ED will also change. If the energy density exceeds the scope of the set ones, the efficiency also will be changed with it.

Figure 3:
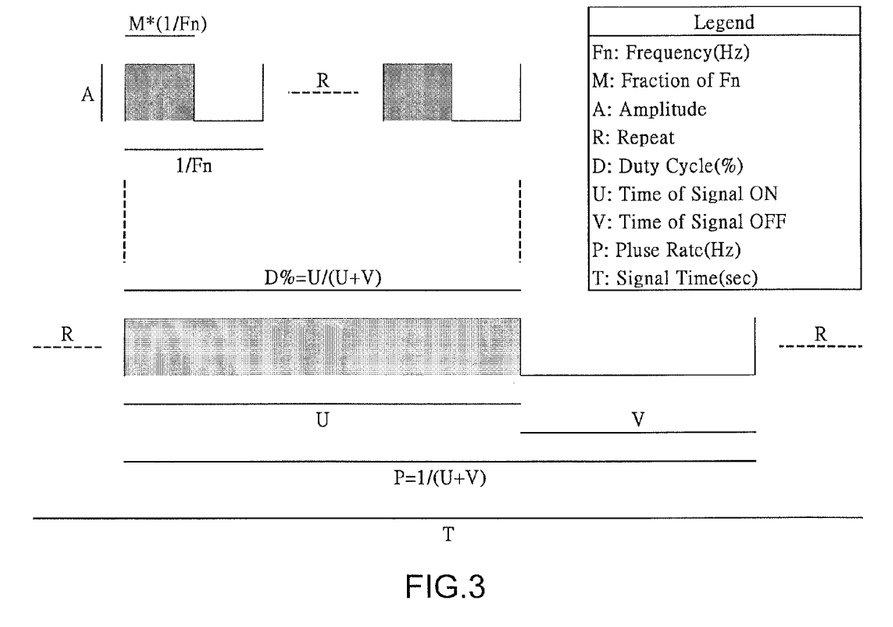
FIG. 3 is a schematic view of wave form of a duty cycle of the present invention.

As shown in FIGS. 3 and 9, in one embodiment of the present invention, the energy wave is a square wave, D is the duty cycle, T is effect time of a single frequency, D % is emission rate of duty cycle of each base frequency and equal to U/(U+V). In the embodiment of present invention, we set the wave emission rate to be 70% for each duty cycle. U is the part of 70% which represents the time of signal outputs of positive potential in square wave, and V is the part of 30% which represents the time of signal outputs of 0 potential in OFF status. P represents a Pulse Rate (Hz) of frequency, P=1/(U+V). TT is the total time of emission period based on each base frequency in each duty cycle. In FIG. 9, the normalized percentages (normal) in each order, is the ratio between the ED in the effect period based on each base frequency and the sum of ED of the whole effect periods based on whole base frequencies from order 1 to 50 shown in FIG. 9.

Referring to FIG. 9, during the first energy wave generation period, the control mode of the 1st frequency is fixed frequency sweep mode, which sets a fixed 1st base frequency within 22000~22200 Hz (preferably 22107), emission rate (D %)=70% for a duty cycle, sweep bandwidth (Width) (m)=0 Hz and total time of emission (TT)=2 seconds for a duty cycle; the control mode of the 2nd frequency is fixed frequency sweep mode, which sets a fixed 2nd base frequency within 14300~15700 Hz (preferably 15036), D %=70%, Width (m)=0 Hz and TT=7 secs for a duty cycle; the control mode of the 3rd frequency is fixed frequency sweep mode, which sets a fixed 3rd base frequency within 9500~10500 Hz (preferably 10000), D %=70%, Width (m)=0 Hz and TT=12 secs for a duty cycle; and the control mode of the 4th frequency is fixed frequency sweep mode, which sets a fixed 4th base frequency within 4750~5250 Hz (preferably 5000), D %=70%, Width (m)=0 Hz and TT=21 secs for a duty cycle; the control mode of the 4th frequency is fixed frequency sweep mode, which sets a fixed 5th base frequency within 4220~4640 Hz (preferably 4442), D %=70%, Width (m)=0 Hz and TT=23 secs for a duty cycle; and the control mode of the 6th frequency is frequency sweep increasing mode, which sets effect frequencies increasingly adjusted and based on a 6th base frequency between 3025~3325 Hz (preferably 3175) with emission rate (D %) equal to 70%, sweep bandwidth (Width) equal to 2 Hz, adjusted bandwidth equal to 1 Hz, and total time of emission (TT) equal to 27 secs for a duty cycle.

Figure 4:
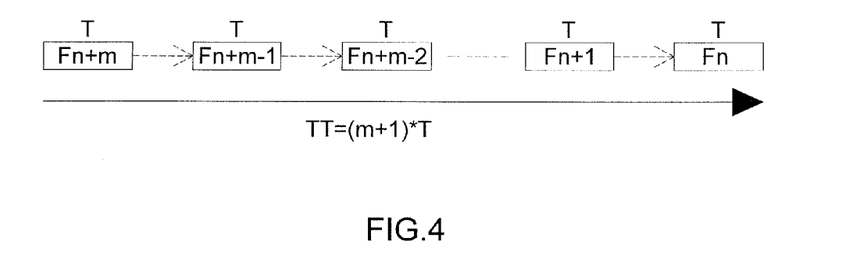
FIG. 4 is a schematic view of distribution of effect frequencies calculated by the sweep decreasing mode of the present invention.

Referring to FIG. 4, during the second energy wave generation period, the control mode of the 7th frequency is fixed frequency sweep mode, which sets a fixed 7th base frequency between 2400~2425 Hz (preferably 2411 Hz), emission rate (D %)=70% for a duty cycle, sweep bandwidth (Width) (m)=0 Hz and total time of emission (TT)=31 seconds for a duty cycle; the control mode of the 8th frequency is fixed frequency sweep mode, which sets a fixed 8th base frequency between 1955~1985 Hz (preferably 1972 Hz), D %=70%, Width (m)=0 Hz and TT=33 secs for a duty cycle; the control mode of the 9th frequency is fixed frequency sweep mode, which sets a fixed 9th base frequency between 1800~1850 Hz (preferably 1823 Hz), D %=70%, Width (m)=0 Hz and TT=34 secs for a duty cycle; and the control mode of the 10th frequency is fixed frequency sweep mode, which sets a fixed 10th base frequency between 1620~1665 Hz (preferably 1644 Hz), D %=70%, Width (m)=0 Hz and TT=36 secs for a duty cycle; and the control mode of the 11th frequency is frequency sweep decreasing mode, which sets effect frequencies decreasingly adjusted and based on a 11th base frequency between 1520~1580 Hz (preferably 1550 Hz) with emission rate (D %) equal to 70%, sweep bandwidth (Width) equal to 2 Hz, adjusted bandwidth equal to 1 Hz, and total time of emission (TT) equal to 36 secs for a duty cycle.

Referring to FIG. 9, during the third energy wave generation period, the control mode of the 12th frequency is a frequency sweep increasing mode, which sets effect frequencies decreasingly adjusted and based on a 12th base frequency between 510 Hz~532 Hz (preferably 522 Hz) with D %=70%, Width (m)=2 Hz and TT=51 secs for a duty cycle; the control mode of the 13th frequency is a frequency sweep decreasing mode, which sets effect frequencies decreasingly adjusted and based on a 13th base frequency between 500~520 Hz (preferably 510 Hz) with emission rate (D %) equal to 70%, sweep bandwidth (Width) equal to 2 Hz, adjusted bandwidth equal to 1 Hz, and total time of emission (TT) equal to 51 seconds for a duty cycle; the control mode of the 14th frequency is a frequency sweep increasing mode, which sets effect frequencies increasingly adjusted and based on a 14th base frequency between 450 hz~480 Hz (preferably 464 Hz) with D %=70%, Width (m)=5 Hz, adjusted bandwidth=1 Hz and TT=54 secs for a duty cycle; the control mode of the 15th frequency is a fixed frequency sweep mode, which sets a fixed 15th base frequency between 430 hz~460 Hz (preferably 442 Hz) with D %=70%, Width (m)=0 Hz, adjusted bandwidth=1 Hz and TT=53 secs for a duty cycle.

Referring to FIG. 4, during the fourth energy wave generation period, the control mode of the 16th frequency is a frequency spread contract mode, which sets effect frequencies decreasing and increasing alternately adjusted to contract based on a 16th base frequency between 845~880 Hz (preferably 860 Hz) with D %=70%, Width (m)=7 Hz and TT=45 secs for a duty cycle; the control mode of the 17th frequency is a sweep increasing mode, which sets effect frequencies increasingly adjusted based on a 17th base frequency between 811~840 Hz (preferably 823 Hz) with D %=70%, Width (m)=8 Hz, adjusted bandwidth=1 Hz and TT=45 secs for a duty cycle; the control mode of the 18th frequency is a frequency spread contract mode, which sets effect frequencies decreasing and increasing alternately adjusted to contract based on a 18th base frequency between 791~812 Hz (preferably 801 Hz) with D %=70%, Width (m)=6 Hz, adjusted bandwidth=1 Hz and TT=39 secs for a duty cycle; the control mode of the 19th frequency is a frequency spread contract mode, which sets effect frequencies decreasing and increasing alternately adjusted to contract based on a 19th base frequency between 770~790 Hz (preferably 781 Hz) with D %=70%, Width (m)=7 Hz and TT=45 secs for a duty cycle.

Referring to FIG. 4, during the fifth energy wave generation period, the control mode of the 20th frequency is a frequency sweep increasing mode, which sets effect frequencies increasingly adjusted and based on a 20th base frequency between 339~360 Hz (preferably 346 Hz) with D %=70%, Width (m)=9 Hz, adjusted bandwidth=1 Hz and TT=60 secs for a duty cycle; the control mode of the 21st frequency is a frequency spread contract mode, which sets effect frequencies decreasing and increasing alternately adjusted to contract based on a 21st base frequency between 328~350 Hz (preferably 338 Hz) with D %=70%, Width (m)=7 Hz, adjusted bandwidth=1 Hz and TT=60 secs for a duty cycle; the control mode of the 22nd frequency is a frequency spread contract mode, which sets effect frequencies decreasing and increasing alternately adjusted to contract based on a 22nd base frequency between 238~260 Hz (preferably 248 Hz) with D %=70%, Width (m)=6 Hz, adjusted bandwidth=1 Hz and TT=65 secs for a duty cycle.

Referring to FIG. 4, during the sixth energy wave generation period, the control mode of the 23rd frequency is a frequency sweep decreasing mode, which sets effect frequencies decreasing adjusted and based on a 23rd base frequency between 26~42 Hz (preferably 33 Hz) with D %=70%, Width (m)=2 Hz, adjusted bandwidth=1 Hz and TT=88 secs for a duty cycle; the control mode of the 24th frequency is a fixed frequency sweep mode, which sets effect frequencies decreasing and increasing alternately adjusted to contract based on a 30th base frequency between 5~23 Hz (preferably 13 Hz) with D %=70%, Width (m)=7 Hz, adjusted bandwidth=1 Hz and TT=105 secs for a duty cycle.

Referring to FIG. 9, the control mode of the fixed frequency sweep mode depicted in the present invention means the frequency of each treatment functioning at a fixed frequency until the total time (TT) of the base frequency effect period ends. In the case of the first energy wave generation period, for example, assuming that the first frequency is 22107 Hz, then the first frequency is fixed at 22107 Hz until the total time of the frequency reaches 2 seconds. After that, it goes to the next base frequency effect period, and so on. Because there is no value change of the frequency range for the fixed frequency sweep mode, therefore, the sweep bandwidth is 0 Hz.

Referring to FIGS. 4 and 9, the control mode of the aforementioned frequency sweep decreasing mode is to control the system to emit the energy wave by frequency decreasing distribution with an adjusted bandwidth in the predetermined sweep bandwidth. The calculation of the value change of the sweep decreasing mode depicted in the present invention is described as below. The first output frequency is calculated as a base frequency (Fn) plus a sweep bandwidth (m), and the second output frequency is calculated as the first output frequency minus an adjusted bandwidth (such as 1 Hz). When the current output frequency is equal to the base frequency (Fn), the current output frequency will be the last output frequency. In the case of the 11th base frequency, for example, the base frequency is 1550 Hz with sweep bandwidth (Width) (m) 2 Hz. Based on the above formula, two frequencies can be obtained, and the sequence of the output effect frequencies are 1552 Hz, 1551 Hz and 1550 Hz respectively. Each single-frequency's effect time (T) in the sweep decreasing mode is 12 seconds, so the total time of the two frequencies (TT) is 36 seconds, i.e., TT=(m+1)×T.

Figure 5:
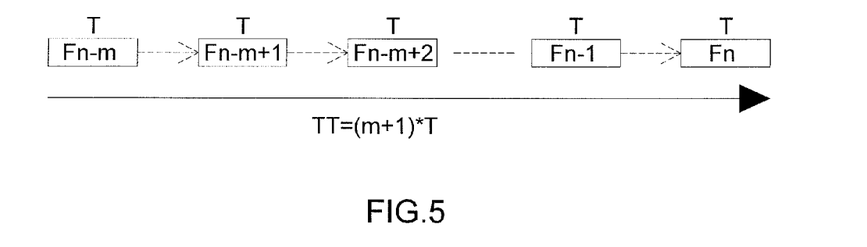
FIG. 5 is a schematic view of distribution of effect frequencies calculated by the sweep increasing mode of the present invention.

Referring to FIGS. 5 and 9, the control mode of the aforementioned frequency sweep increasing mode is to control the system to emit the energy wave by frequency increasing distribution with an adjusted bandwidth in a predetermined sweep bandwidth. The calculation of the value change of the sweep increasing mode depicted in the present invention is described as below. The first output frequency is calculated as a base frequency (Fn) minus the sweep bandwidth (m), and the second output frequency is calculated as the first output frequency plus an adjusted bandwidth (such as 1 Hz). When the current output frequency is equal to the base frequency (Fn), the current output frequency will be the last output frequency. In the case of the 6th base frequency, for example, the base frequency is 3175 Hz with the sweep bandwidth (Width)=2 Hz and the adjusted bandwidth=1 Hz. Based on the above formula, three frequencies can be obtained, and the sequence of the output effect frequencies are 3173 Hz, 3174 Hz and 3175 Hz respectively. Each single-frequency's effect time (T) in the sweep increasing mode is 9 seconds, so that the total time of the three effect frequencies (TT) is 27 seconds, i.e., TT=(m+1)×T.

Figure 6:
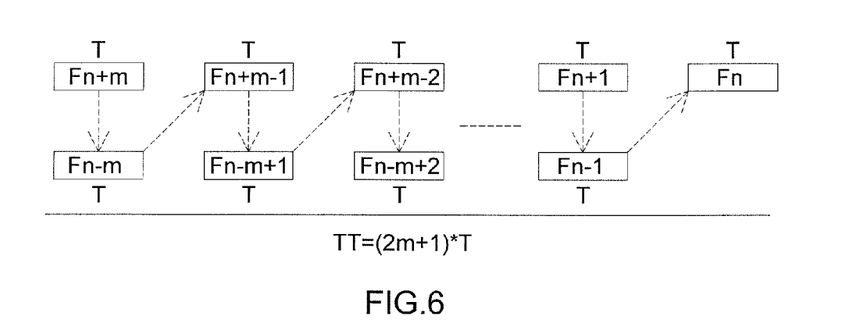
FIG. 6 is a schematic view of distribution of effect frequencies calculated by the spread contract mode of the present invention.

Referring to FIGS. 6 and 9, the control mode of the aforementioned frequency spread contract mode is to control the system to emit the energy wave by alternating increasing frequency and decreasing frequency distribution with an adjusted bandwidth in a predetermined sweep bandwidth. The calculation of the value change of the spread contract mode depicted in the present invention is described as below. The first output frequency is calculated as a base frequency (Fn) minus a sweep bandwidth (m), the second output frequency is calculated as a base frequency (Fn) plus a sweep bandwidth (m), the third output frequency is calculated as the first output frequency plus an adjusted bandwidth (such as 1 Hz), the fourth output frequency is calculated as the second output frequency minus an adjusted bandwidth (such as 1 Hz), and so on. When the current output frequency is equal to the base frequency (Fn), the current output frequency will be the last output frequency. In the case of the 16th base frequency, for example, the 16th base frequency is 860 Hz with the sweep bandwidth (m)=7 Hz and the adjusted bandwidth=1 Hz. Based on the above formula, fifteen frequencies can be obtained, and the sequence of the output effect frequencies are 867 Hz, 853 Hz, 866 Hz, 854 Hz, 865 Hz, 855 Hz, 864 Hz, 856 Hz, 863 Hz, 857 Hz, 862 Hz, 858 Hz, 861 Hz, 859 Hz and 860 Hz respectively. Each single-frequency's effect time (T) is 3 seconds, so that the total time of the fifteen frequencies (TT) is 45 seconds, i.e., TT=(2 m+1)×T.

Figure 7:
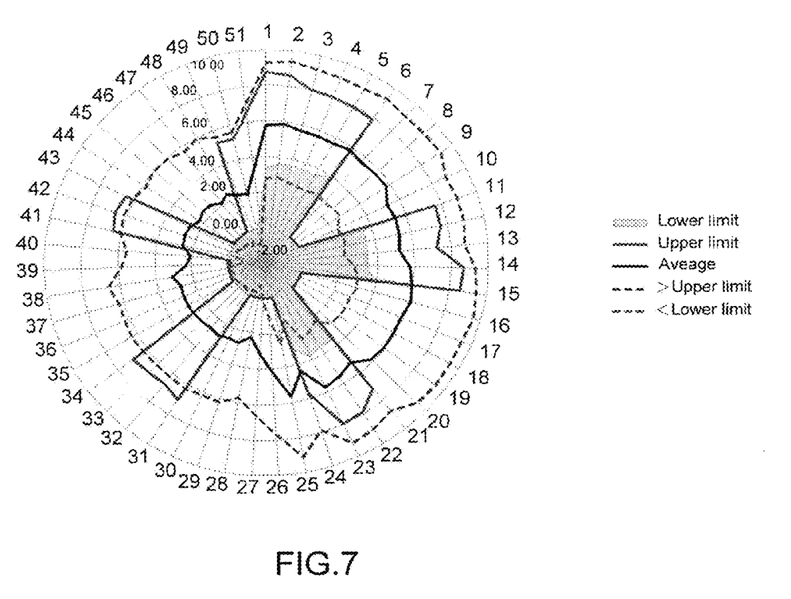
FIG. 7 is a schematic view of distribution of energy density on linear timeline of the present invention.
Figure 8:
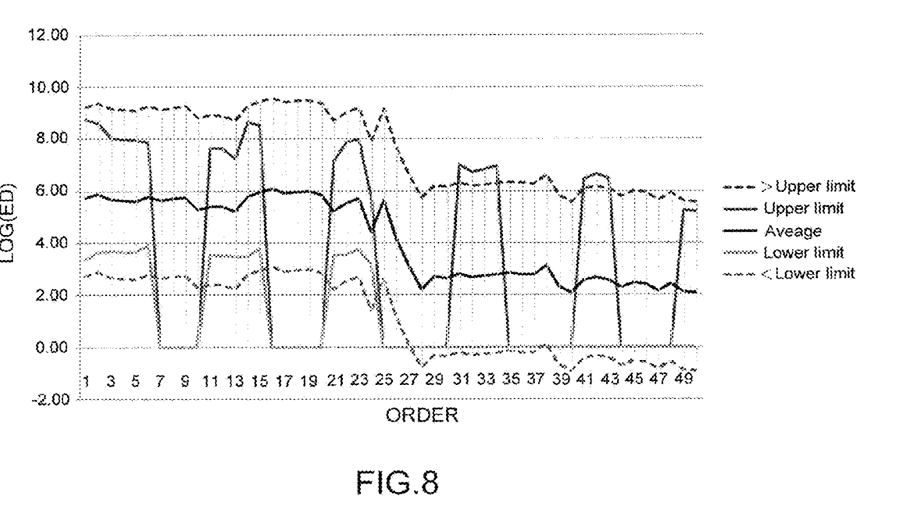
FIG. 8 is a schematic view of distribution of energy density on circular timeline of the present invention.

FIG. 7 shows the distribution schematic of the energy density in energy wave's frequency control mode against the linear timeline in the present invention. Wherein, the upper limit and the lower limit shown in FIG. 7 represent the upper range and the lower range of the energy density against the timeline mentioned above in accordance with the present invention. FIG. 8 shows the distribution schematic of the energy density in energy wave's frequency control mode against the annular timeline in the present invention.

Wherein, the central portion is the average distribution of the energy density against the timeline mentioned above in accordance with the present invention.

On the chart shown in FIG. 9, the base frequency distributions of first to sixth energy wave generation periods are from orders 1-6, 11-15, 21-24, 31-34, 41-43 and 49-50 chronologically respectively.

In the present embodiment, besides above frequency treatment period, the energy wave's frequency control mode also includes five non-energy periods, i.e., from the first to the fifth non-energy periods generated between every two adjacent energy density from the first to the ninth periods correspondingly. The total time of the first to eighth non-energy periods are 149, 259, 340, 346 and 347 seconds respectively. The energy wave generator 10 generates various frequencies in each non-energy periods and filters the frequency to have non-energy. Referring to FIG. 9, the first to the eighth non-energy periods is chronologically generated in-between order 7-10, order 16-20, order 25-30, order 35-40 and order 44-48 in sequence.

While we have shown and described the embodiment in accordance with the present invention, it should be clear to those skilled in the art that further embodiments may be made without departing from the scope of the present invention.

What is claimed is:

1. A system for promoting immunity of animals or human, comprising an energy wave generator having an energy wave's frequency control mode for controlling and generating energy waves; the energy wave's frequency control mode comprising multiple controls in multiple energy wave generation periods respectively, the multiple controls acting the energy wave generator to generate and emit energy waves each with a corresponding energy density having a value between 0.00~8.93 by a corresponding base frequency between 1~22200 Hz to effect on bodies of animals or human so as to promote immunities of the animals or human; the control modes being at least one fixed frequency sweep mode and at least one adjusted frequency sweep mode; the at least one adjusted frequency sweep mode being a sweep decreasing mode, a spread contract mode or a sweep increasing mode; the energy wave generator emitting energy waves to have a frequency decreasing distribution in a predetermined sweep bandwidth by a predetermined adjusted bandwidth in the sweep decreasing mode, to have a frequency increasing distribution in a predetermined sweep bandwidth by a predetermined adjusted bandwidth in the sweep increasing mode, and to have an increasing frequency and a decreasing frequency alternately in a predetermined sweep bandwidth by a predetermined adjusted bandwidth in the spread contract mode; the energy density of each energy wave being calculated by the following formula: $ED = \log 10 \, (\text{freq.} \times D\% \times (2 \, \text{Width} + 1) \times (TT) + 1)$, wherein freq., Width, D % and TT represent the base frequency, the predetermined sweep bandwidth, an emission rate and a total time of emission in a duty cycle of the base frequency respectively.

2. The system as claimed in claim 1, wherein there is at least one non-energy period between every two adjacent periods of the multiple energy wave generation periods, the energy wave generator generates at least one base frequency in each non-energy periods and filters the at least one base frequency to have non-energy.

3. The system as claimed in claim 1, wherein the multiple controls act the energy wave generator in two energy wave generation periods to sequentially outputs two sets of energy waves with corresponding two sets of energy densities between 3.37~8.73 and 0.00~5.26 respectively.

4. The system as claimed in claim 3, wherein the D %=70%, the Width is 0, 2 or 7 Hz, and the TT=2, 7, 12, 21, 23, 27, 88 or 105 secs; the base frequencies are between 22000~22200 Hz, 14300~15700 Hz, 9500~10500 Hz, 4750~5250 Hz, 4220~4640 Hz, 3025~3325 Hz, 31~35 Hz or 12~14 Hz.

5. The system as claimed in claim 1, wherein the multiple controls act the energy wave generator in the multiple energy wave generation periods to sequentially outputs multiple sets of energy waves with corresponding multiple sets of energy densities between 3.37~8.73, 3.16~7.96, 0.00~6.66 and 0.00~5.26 respectively.

6. The system as claimed in claim 5, wherein the D %=70%, the Width is 0, 2, 5, 6, 7 or 9 Hz, and the TT=2, 7, 12, 21, 23, 27, 51, 53, 54, 60, 65, 88 or 105 secs; the base frequencies are between 22000~22200 Hz, 14300~15700 Hz, 9500~10500 Hz, 4750~5250 Hz, 4220~4640 Hz, 3025~3325 Hz, 510~532 Hz, 500~520 Hz, 450~480 Hz, 430~460 Hz, 339~360 Hz, 328~350 Hz, 238~260 Hz, 26~42 Hz or 5~23 Hz.

7. The system as claimed in claim 1, wherein the multiple controls are six sets, the multiple energy wave generation periods are six sequentially from a 1st to sixth corresponding to the six sets of controls, so as to act the energy wave generator to sequentially emit six sets of energy waves from a 1st to sixth with corresponding six sets of energy densities between 3.37~8.73, 3.46~8.63, 3.16~7.96, 0.00~7.01, 0.00~6.66 and 0.00~5.26 respectively.

8. The system as claimed in claim 7, wherein there are five non-energy periods from a first to an fifth non-energy periods sequentially between every two adjacent periods of the multiple energy wave generation periods, the energy wave generator generates various frequencies in each non-energy periods and filters the various frequencies to have non-energy correspondingly.

9. The system as claimed in claim 8, wherein the total time of the first to fifth non-energy periods are 149, 259, 340, 346 and 347 seconds respectively, the energy wave generator generates various frequencies in each non-energy periods and filters the various frequencies to have non-energy.

10. The system as claimed in claim 7, wherein in the first energy wave generation period, the first sets of energy waves are sequentially a 1st to a 6th energy waves with a 1st to a 6th energy densities by a 1st to a 6th base frequencies respectively, the 1st energy density is between 3.37~8.73, the 2nd energy density is between 3.65~8.60, the 3rd energy density is between 3.69~8.03, the 4th energy density is between 3.65~7.98, and the 5th energy density is between 3.64~7.93, and the 6th energy density is between 3.94~7.88; in the second energy wave generation period, the second sets of energy waves are sequentially a 7th to a 11th energy waves with corresponding a 7th to a 11th energy densities by a 7th to a 11th base frequencies respectively, the 7th energy density is between 3.54~7.62, the 8th energy density is between 3.49~7.63, the 9th energy density is between 3.48~7.25, the 10th energy density is between 3.46~8.63, the 11th energy density is between 3.80~8.55; in the third energy wave generation period, the third sets of energy waves are sequentially a 12th to a 15th energy waves with a 12th to a 15th energy densities by a 12th to a 15th base frequencies respectively, the 12th energy density is between 3.56~7.12, the 13th energy density is between 3.55~7.88, the 14th energy density is between 3.77~7.96, the 15th energy density is between 3.16~5.73; in the fourth energy wave generation period, the fourth sets of energy waves are sequentially a 16th to a 19th energy waves with a 16th to a 19th energy densities by a 16th to a 19th base frequencies respectively, the 16th energy density is between 0.00~7.01, the 17th energy density is between 0.00~6.71, the 18th energy density is between 0.00~6.82, the 19th energy density is between 0.00~6.96; in the fifth energy wave generation period, the fifth sets of energy waves are sequentially a 20th to a 22nd energy waves with a 20th to a 22nd energy densities by a 20th to a 22nd base frequencies respectively, the 20th energy density is between 0.00~6.45, the 21st energy density is between 0.00~6.66, the 22nd the energy density is between 0.00 and 6.46; in the sixth energy wave generation period, the sixth sets of energy waves are sequentially a 23rd to a 24th energy waves with a 23rd to a 24th energy densities by a 23rd to a 24th base frequencies respectively, the 23rd energy density is between 0.00~5.26, the 24th energy density is between 0.00~5.20.

11. The system as claimed in claim 10, wherein the control modes based on the 1st to 5th, 7th to 10th and 15th base frequencies are fixed frequency sweep modes respectively, the D %=70%, the Width=0 Hz, and the TT=2, 7, 12, 21, 23, 31, 33, 34, 36 and 53 secs respectively; the control modes based on the 11th, 13th and 23rd base frequencies are sweep decreasing modes respectively, the D %=70%, the Width=2, 2 and 7 Hz, and the TT=36, 51 and 88 secs respectively; the control mode based on the 6th, 12th, 14th, 17th and 20th base frequencies are sweep increasing modes respectively, the D %=70%, the Width=2, 2, 5, 8 and 9 Hz respectively, and the TT=27, 51, 54, 45 and 60 secs respectively; the control mode based on the 16th, 18th, 19th, 21st, 22nd and 24th base frequencies are spread contract modes respectively, the D %=70%, the Width=7, 6, 7, 7, 6 and 7 Hz, and the TT=45, 39, 45, 60, 65 and 105 secs respectively; the 1st to 24th base frequencies are between 22000~22200 Hz, 14300~15700 Hz, 9500~10500 Hz, 4750~5250 Hz, 4220~4640 Hz, 3025~3325 Hz, 2400~2425 Hz, 1955~1985 Hz, 1800~1850 Hz, 1620~1665 Hz, 1520~1580 Hz, 510~532 Hz, 500~520 Hz, 450~480 Hz, 430~460 Hz, 845~880 Hz, 811~840 Hz, 791~812 Hz, 770~790 Hz, 339~360 Hz, 328~350 Hz, 238~260 Hz, 26~42 Hz and 5~23 Hz respectively.

12. The system as claimed in claim 11, wherein multiple effect frequencies are produced and calculated by one predetermined adjusted bandwidth equal to 1 Hz based on each base frequency in each sweep decreasing mode; multiple effect frequencies are produced and calculated by one predetermined adjusted bandwidth equal to 1 Hz based on each base frequency in each spread contract mode; multiple frequencies are produced and calculated by one predetermined adjusted bandwidth equal to 1 Hz based on each base frequency in each sweep increasing mode; in the sweep decreasing mode, the first output frequency of the multiple frequencies is calculated as the base frequency plus the Width, the second output frequency of the multiple frequencies is calculated as the first output frequency minus the predetermined adjusted bandwidth, and when a current output frequency of the multiple frequencies is equal to the base frequency, the current output frequency is a last output frequency; in the spread contract mode, the first output frequency of the multiple frequencies is calculated as the base frequency minus the Width, the second output frequency of the multiple frequencies is calculated as a base frequency plus the Width, the third output frequency of the multiple frequencies is calculated as the first output frequency plus the predetermined adjusted bandwidth, the fourth output frequency of the multiple frequencies is calculated as the second output frequency minus the predetermined adjusted bandwidth and so on, and when the current output frequency of the multiple frequencies is equal to the base frequency, the current output frequency is the last output frequency; in the sweep increasing mode, the first output frequency of the multiple frequencies is calculated as the base frequency minus the sweep bandwidth, the second output frequency of the multiple frequencies is calculated as the first output frequency plus the predetermined adjusted bandwidth, and when the current output frequency of the multiple frequencies is equal to the base frequency, the current output frequency is the last output frequency.

13. A method for promoting immunity of animals or human, comprising the steps of: providing a system as claimed in claim 1; the multiple controls acting the energy wave generator to generate and emit energy waves each with a corresponding energy density having a value between 0.00~8.93 by a corresponding base frequency between 1~22200 Hz to effect on bodies of animals or human so as to promote immunities of the animals or human; the control modes being multiple fixed frequency sweep modes and multiple adjusted frequency sweep modes; the multiple adjusted frequency sweep modes being at least one sweep decreasing mode, at least one spread contract mode and at least one sweep increasing mode; the energy wave generator emitting energy waves to have a frequency decreasing distribution in a predetermined sweep bandwidth with an adjusted bandwidth in the sweep decreasing mode, to have a frequency increasing distribution in a predetermined sweep bandwidth with an adjusted bandwidth in the sweep increasing mode, and to have an increasing frequency and a decreasing frequency alternately in a predetermined sweep bandwidth with an adjusted bandwidth in the spread contract mode; the energy density of each energy wave being calculated by the following formula: ED=log 10 (freq.×D %×(2 Width+1)×(TT)+1) wherein freq., Width, D % and TT represent the base frequency, the predetermined sweep bandwidth, an emission rate and a total time of emission in a duty cycle of the base frequency respectively.

14. The method as claimed in claim 13, wherein the multiple controls are six sets, the multiple energy wave generation periods are six sequentially from a 1st to sixth corresponding to the six sets of controls, so as to act the energy wave generator to sequentially emit six sets of energy waves from a 1st to sixth with corresponding six sets of energy densities between 3.37~8.73, 3.46~8.63, 3.16~7.96, 0.00~7.01, 0.00~6.66 and 0.00~5.26 respectively.

15. The method as claimed in claim 14, wherein there are five non-energy periods from a first to an fifth non-energy periods sequentially between every two adjacent periods of the multiple energy wave generation periods, the energy wave generator generates various frequencies in each non-energy periods and filters the various frequencies to have non-energy correspondingly.

16. The method as claimed in claim 15, wherein the total time of the first to fifth non-energy periods are 149, 259, 340, 346 and 347 seconds respectively, the energy wave generator generates various frequencies in each non-energy periods and filters the various frequencies to have non-energy.

17. The method as claimed in claim 14, wherein in the first energy wave generation period, the first sets of energy waves are sequentially a 1st to a 6th energy waves with a 1st to a 6th energy densities by a 1st to a 6th base frequencies respectively, the 1st energy density is between 3.37~8.73, the 2nd energy density is between 3.65~8.60, the 3rd energy density is between 3.69~8.03, the 4th energy density is between 3.65~7.98, and the 5th energy density is between 3.64~7.93, and the 6th energy density is between 3.94~7.88;

in the second energy wave generation period, the second sets of energy waves are sequentially a 7th to a 11th energy waves with corresponding a 7th to a 11th energy densities by a 7th to a 11th base frequencies respectively, the 7th energy density is between 3.54~7.62, the 8th energy density is between 3.49~7.63, the 9th energy density is between 3.48~7.25, the 10th energy density is between 3.46~8.63, the 11th energy density is between 3.80~8.55; in the third energy wave generation period, the third sets of energy waves are sequentially a 12th to a 15th energy waves with a 12th to a 15th energy densities by a 12th to a 15th base frequencies respectively, the 12th energy density is between 3.56~7.12, the 13th energy density is between 3.55~7.88, the 14th energy density is between 3.77~7.96, the 15th energy density is between 3.16~5.73; in the fourth energy wave generation period, the fourth sets of energy waves are sequentially a 16th to a 19th energy waves with a 16th to a 19th energy densities by a 16th to a 19th base frequencies respectively, the 16th energy density is between 0.00~7.01, the 17th energy density is between 0.00~6.71, the 18th energy density is between 0.00·6.82, the 19th energy density is between 0.00~6.96; in the fifth energy wave generation period, the fifth sets of energy waves are sequentially a 20th to a 22nd energy waves with a 20th to a 22nd energy densities by a 20th to a 22nd base frequencies respectively, the 20th energy density is between 0.00~6.45, the 21st energy density is between 0.00~6.66, the 22nd the energy density is between 0.00 and 6.46; in the sixth energy wave generation period, the sixth sets of energy waves are sequentially a 23rd to a 24th energy waves with a 23rd to a 24th energy densities by a 23rd to a 24th base frequencies respectively, the 23rd energy density is between 0.00~5.26, the 24th energy density is between 0.00~5.20.

18. The method as claimed in claim 17, wherein the control modes based on the 1st to 5th, 7th to 10th and 15th base frequencies are fixed frequency sweep modes respectively, the D %=70%, the Width=0 Hz, and the TT=2, 7, 12, 21, 23, 31, 33, 34, 36 and 53 secs respectively; the control modes based on the 11th, 13th and 23rd base frequencies are sweep decreasing modes respectively, the D %=70%, the Width=2, 2 and 7 Hz, and the TT=36, 51 and 88 secs respectively; the control mode based on the 6th, 12th, 14th, 17th and 20th base frequencies are sweep increasing modes respectively, the D %=70%, the Width=2, 2, 5, 8 and 9 Hz respectively, and the TT=27, 51, 54, 45 and 60 secs respectively; the control mode based on the 16th, 18th, 19th, 21st, 22nd and 24th base frequencies are spread contract modes respectively, the D %=70%, the Width=7, 6, 7, 7, 6 and 7 Hz, and the TT=45, 39, 45, 60, 65 and 105 secs respectively; the 1st to 24th base frequencies are between 22000~22200 Hz, 14300~15700 Hz, 9500~10500 Hz, 4750~5250 Hz, 4220~4640 Hz, 3025~3325 Hz, 2400~2425 Hz, 1955·1985 Hz, 1800~1850 Hz, 1620~1665 Hz, 1520~1580 Hz, 510~532 Hz, 500~520 Hz, 450~480 Hz, 430~460 Hz, 845·880 Hz, 811~840 Hz, 791~812 Hz, 770~790 Hz, 339~360 Hz, 328~350 Hz, 238~260 Hz, 26~42 Hz and 5~23 Hz respectively.

19. The method as claimed in claim 18, wherein multiple frequencies are produced and calculated by one predetermined adjusted bandwidth equal to 1 Hz based on each base frequency in each sweep decreasing mode; multiple frequencies are produced and calculated by one predetermined adjusted bandwidth equal to 1 Hz based on each base frequency in each spread contract mode; multiple frequencies are produced and calculated by one predetermined adjusted bandwidth equal to 1 Hz based on each base frequency in each sweep increasing mode; in the sweep decreasing mode, the first output frequency of the multiple frequencies is calculated as the base frequency plus the Width, the second output frequency of the multiple frequencies is calculated as the first output frequency minus the predetermined adjusted bandwidth, and when a current output frequency of the multiple frequencies is equal to the base frequency, the current output frequency is a last output frequency; in the spread contract mode, the first output frequency of the multiple frequencies is calculated as the base frequency minus the Width, the second output frequency of the multiple frequencies is calculated as a base frequency plus the Width, the third output frequency of the multiple frequencies is calculated as the first output frequency plus the predetermined adjusted bandwidth, the fourth output frequency of the multiple frequencies is calculated as the second output frequency minus the predetermined adjusted bandwidth and so on, and when the current output frequency of the multiple frequencies is equal to the base frequency, the current output frequency is the last output frequency; in the sweep increasing mode, the first output frequency of the multiple frequencies is calculated as the base frequency minus the sweep bandwidth, the second output frequency of the multiple frequencies is calculated as the first output frequency plus the predetermined adjusted bandwidth, and when the current output frequency of the multiple frequencies is equal to the base frequency, the current output frequency is the last output frequency.

\* \* \* \* \*